(12) United States Patent
Rönnberg

(10) Patent No.: US 6,241,716 B1
(45) Date of Patent: Jun. 5, 2001

(54) WAIST BELT FOR ABSORBENT ARTICLES

(75) Inventor: Peter Rönnberg, Mölndal (SE)

(73) Assignee: SCA Hygiene Products Aktiebolag, Gothenburg (SE)

( * ) Notice: Subject to any disclaimer, the term of this patent is extended or adjusted under 35 U.S.C. 154(b) by 0 days.

(21) Appl. No.: 09/117,354

(22) PCT Filed: Mar. 4, 1997

(86) PCT No.: PCT/SE97/00370

§ 371 Date: Jul. 28, 1998

§ 102(e) Date: Jul. 28, 1998

(87) PCT Pub. No.: WO97/33547

PCT Pub. Date: Sep. 18, 1997

(30) Foreign Application Priority Data

Mar. 13, 1996 (SE) .................................................. 9600965

(51) Int. Cl.[7] ....................................................... A61F 13/15
(52) U.S. Cl. .......................... 604/391; 604/387; 604/389; 604/391; 604/392; 604/385.01
(58) Field of Search ................................. 604/385.1, 387, 604/389, 391, 392

(56) References Cited

U.S. PATENT DOCUMENTS

| | | | |
|---|---|---|---|
| 3,618,608 | * 11/1971 | Brink | 128/287 |
| 4,402,690 | * 9/1983 | Redfern | 604/391 |
| 4,728,326 | * 3/1988 | Gilles | 604/391 |
| 4,917,693 | * 4/1990 | Terry | 604/385.1 |
| 5,032,119 | * 7/1991 | Hookano | 604/385.1 |
| 5,069,672 | * 12/1991 | Wippler et al. | 604/385.1 |
| 5,106,382 | * 4/1992 | Henry | 604/385.2 |
| 5,106,385 | * 4/1992 | Allen et al. | 604/391 |
| 5,112,326 | * 5/1992 | Quadrini | 604/391 |
| 5,135,522 | * 8/1992 | Fahrenkrug et al. | 604/385.1 |
| 5,261,901 | 11/1993 | Guay . | |
| 5,304,162 | * 4/1994 | Kuen | 604/391 |
| 5,318,555 | * 6/1994 | Siebers et al. | 604/390 |
| 5,370,632 | * 12/1994 | Beplate | 604/385.1 |
| 5,374,262 | * 12/1994 | Keuhn, Jr. et al. | 604/391 |
| 5,386,595 | * 2/1995 | Kuen et al. | 2/400 |
| 5,403,303 | * 4/1995 | Beplate | 604/394 |
| 5,423,789 | * 6/1995 | Kuen | 604/386 |
| 5,445,628 | * 8/1995 | Gipson et al. | 604/392 |

FOREIGN PATENT DOCUMENTS

WO 91/08725 6/1991 (WO) .

* cited by examiner

*Primary Examiner*—Glenn K. Dawson
*Assistant Examiner*—Paul Shanoski
(74) *Attorney, Agent, or Firm*—Young & Thompson

(57) ABSTRACT

A waist belt for supporting disposable-type absorbent articles (7), such as incontinence guards or diapers which comprise a front part, a rear part and an intermediate crotch part, wherein the belt can be fastened to the rear part of the article and when fastened to the rear part of the article comprises two front portions (3, 4) which project out laterally from mutually opposing side edges of the rear part of the article and which can be fastened together through the medium of mechanical fastener elements (12, 14) to form a waist band and which taper towards their respective ends over at least a substantial part of their lengths. Each of the front portions includes first fastener elements (12, 13) which are disposed on the outside of the belt, i.e. that side which faces outwardly in relation to the wearer's body in use, and which extend at least over essentially the whole of the tapering portions of the front portions (10, 11) along the longitudinal symmetry lines thereof. A second fastener element (14) is provided on the inside of one of the front portions at the end part thereof and can be fastened to the first fastener element on the other front portion along a plurality of mutually spaced points along the longitudinal symmetry line of the other front portion.

1 Claim, 3 Drawing Sheets

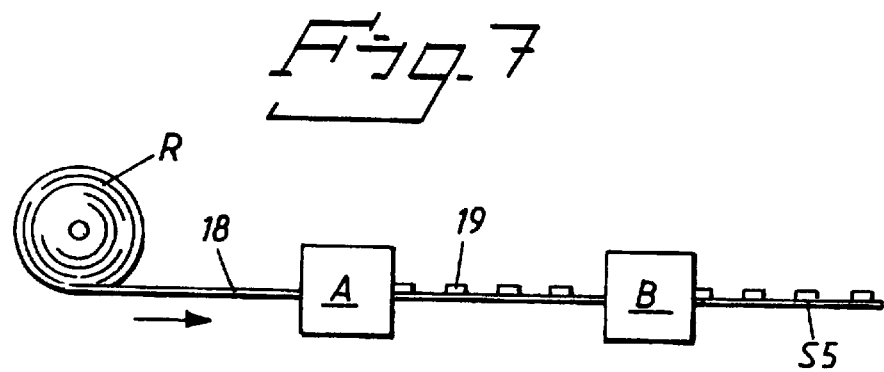
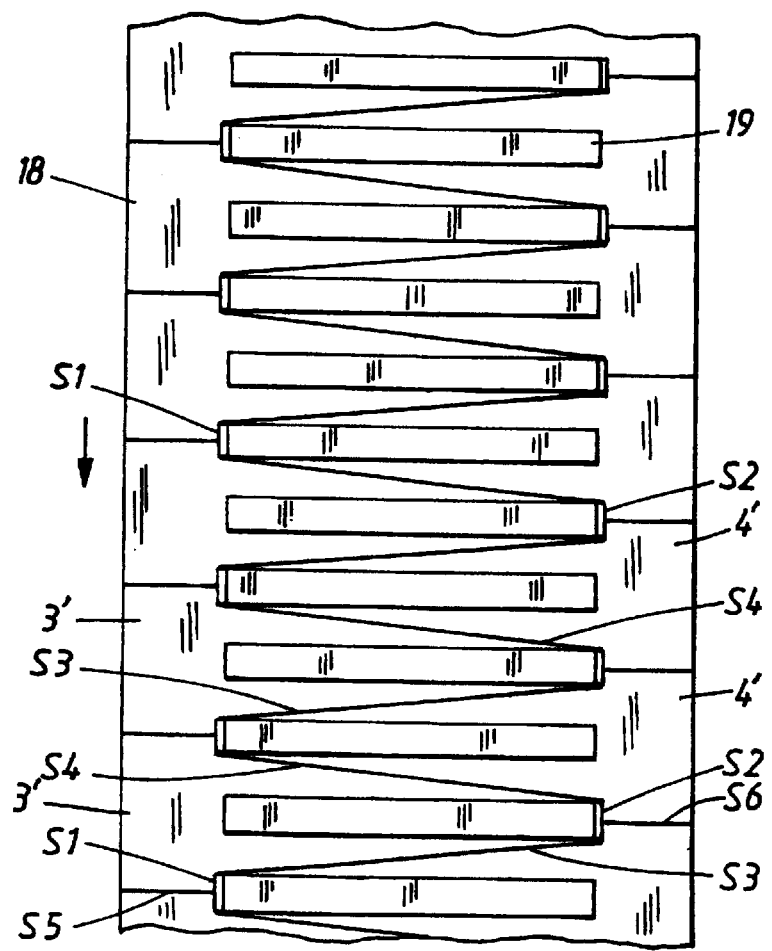

WAIST BELT FOR ABSORBENT ARTICLES

CROSS REFERENCE TO RELATED APPLICATION

This is the 35 USC 371 National Phase of International application PCT/SE97/00370 filed on Mar. 4, 1997, which designated the United States of America.

FIELD OF THE INVENTION

The present invention relates to a waist belt for supporting disposable-type absorbent articles, such as incontinence guards or diapers which comprise a front part, a rear part and an intermediate crotch part, wherein the belt can be fastened to the rear part of the article and when fastened to the rear part of the article comprises two front portions which project out laterally from mutually opposing side edges of the rear part of said article and which can be fastened together through the medium of mechanical fastener elements to form a waist band and which taper towards their respective ends over at least a substantial part of their lengths. The invention also relates to a method of manufacturing such a belt.

BACKGROUND OF THE INVENTION

A waist belt of the type to which the invention refers is known from Applicant's Swedish Application No. 9301631-9. The waist belt described in this publication is relatively expensive to produce, because the loop-bearing material intended for coaction with the hook-bearing means extends over the full extent of the outer surface of the belt, therewith resulting in high material costs.

The main object of the present invention is to reduce the cost of manufacturing a waist belt of this kind, so that a well-functioning disposable waist belt can be produced at a reasonable price.

EP-A2-0,528,282 teaches a diaper in which one end of the outer casing sheets is extended laterally to form extended flaps which by forming a waist band enable the diaper to be placed on a baby with the baby in a standing position. The flaps include mechanical fastener elements which can be fastened to one another and to the side-portions of opposing ends of the diaper. The extended flaps, however, do not support the opposing end of the diaper, which is fastened instead to the side-portions of that diaper end which includes the extended flaps, in a manner which makes it difficult for the baby to reach the fastener points. The problem which the present invention intends to solve is neither mentioned nor indicated in this publication.

SUMMARY OF THE INVENTION

This object is achieved in accordance with the present invention with a waist belt of the aforedefined kind which is characterized in that each of the front portions includes first fastener elements which are disposed on the outside of the belt, i.e. that side which faces outwardly in relation to the wearer's body in use, and which extend at least over essentially the whole of the tapering portions of the front portions along the longitudinal symmetry lines thereof, and in that a second fastener element is provided on the inside of one of the front portions at the end part thereof and which can be fastened to the first fastener element on the other front portion along a plurality of mutually spaced points in the extension of the longitudinal symmetry line of said other front portion. Such a belt can be produced essentially with no waste, and by using separate first fastener elements and placing said elements along the longitudinal symmetry line of the waist belt, it is possible to use fastener elements of optimal width. Furthermore, the belt is easy to handle, by virtue of the fact that the second fastener element is placed at the end portion where the belt is narrowest. This greatly reduces the risk of the first and the second fastener elements being displaced relative to one another in the transverse direction when putting on the belt.

In a preferred embodiment of the invention, the first fastener elements are spaced from the longitudinal edges of the front portion along at least the greatest part of the length of said elements. The first fastener elements are rectangular in shape and have a width of between 20–150 mm, preferably between 30–50 mm. The first fastener elements are produced from a loop-bearing material and the second fastener elements from a hook-bearing material. The front portions are joined firmly to the side-portions of the rear part of an absorbent article and each include a rectangular part of uniform width which is attached to a side-portion of the rear part of an absorbent article, and a uniformly tapering part which projects out from the rectangular part on said front portion and has a greatest width which is smaller than the width of the rectangular part.

The invention also relates to a method of producing tapering waist-belt front portion from a travelling web of material, characterized by placing elongated first fastener elements on and fastening said elements to the web in a mutually sequential row and at a given distance apart with the longitudinal axes of said elements extending perpendicularly to the direction of web travel; cutting the web in accordance with a cutting pattern which includes mutually opposing rows of short-side cuts along each alternate short side of the first fastener elements, said rows being displaced relative to one another in the direction of web travel so that the cuts relating to mutually adjacent first fastener elements will be located along mutually opposing short sides, cuts which extend perpendicularly to the direction of web travel and which extend from the centre of each short-side cut in a direction away from the fastener elements, and connecting cuts which connect the ends of said mutually opposing short-side cuts, wherein second fastener elements intended for coaction with the first fastener elements are fastened to the material web in a row on the side that is opposite to the first fastener elements and centrally opposite those end parts of the first fastener elements that face towards one of the rows of short-side cuts, either before or after attaching the first fastener elements. The method enables front portions intended for integration in the rear part of an incontinence guard or diaper to be produced with practically no waste.

BRIEF DESCRIPTION OF THE DRAWINGS

The invention will now be described with reference to the accompanying drawings, in which

FIG. 7 is a schematic side view of apparatus for producing front portions of a waist belt of the kind illustrated in FIGS. 2 and 3; and FIG. 8 is a sectioned view of a web of material that has passed through the apparatus shown in FIG. 7.

DESCRIPTION OF THE PREFERRED EMBODIMENTS

Figure 1:
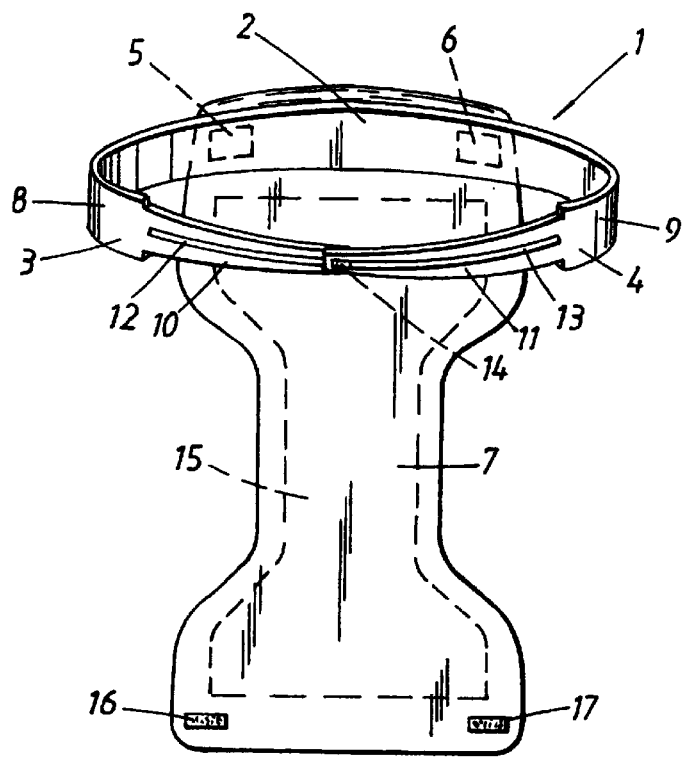
FIG. 1 is a schematic perspective view of a first embodiment of an inventive waist belt and a coacting incontinence guard.

The waist belt 1 illustrated in FIG. 1 is made of a flexible material and includes a rear portion 2 and two front portions 3, 4. The rear portion 2 carries on the outside thereof two mechanical fastener elements 5, 6 for coaction with complementary fastener elements on the rear part of an incontinence guard 7. The mutually complementary mechanical fastener elements may comprise pieces of hook-bearing and loop-bearing material, such as some type of touch and close fasteners or like fasteners. The hook fasteners are preferably mounted on the incontinence guard and the loop fasteners on the belt.

The waist-belt front portions 3, 4 include a relatively broad rear part 8 and 9 respectively, which connect with the rear portions and stretch over the hips of the wearer in use. Tapering or narrowing portions 10 and 11 extend from respective rearparts. Narrow, elongated and rectangular fastener elements 12 and 13 extend along the longitudinal symmetry lines of the tapering portions 10, 11, these fastener elements preferably comprising loop-bearing material. A fastener element 14 complementary to the fastener element 12, preferably a hook-bearing fastener element, is attached to the inside of the tapering portion 11 at the end part thereof. FIG. 1 shows the belt when fastened together, i.e. with the fastener element 14 in engagement with the fastener element 12. As will be understood, because the element 12 extends along substantially the full length of the tapering part 10, the illustrated waist belt can be adjusted to fit around the waist of many users having mutually different waist sizes.

The combination of waist belt 1 and incontinence guard 7 illustrated in FIG. 1 is placed on a standing user in the following way.

The rear edge part of the incontinence guard 7 is first attached to the rear portion of the waist belt through the mutual coaction of fastener elements on the incontinence guard 7 and the belt 1. In the FIG. 1 embodiment, that part of the casing sheet which lies outwardly of the absorbent body 15 is attached to the outside of the belt with the aid of the belt fastener elements 5, 6. Naturally, the fastener elements 5, 6 may be placed on the inside of the belt and the corresponding fastener elements of the incontinence guard on the outside of the rear-edge part, this latter alternative being suitable when those parts of the casing sheets that lie outside the absorbent body are narrower than the rear part of the belt. In the case of the illustrated embodiment, the rear part of the incontinence guard 7 may be attached to the rear part of the waist belt before passing or after having passed the front portions 3, 4 of the belt around the user's waist and fastened said portions together with the aid of the fastener elements 12, 14.

When the waist belt has been fastened around the wearer's waist and the incontinence guard has been fastened to the rear-edge part of the belt, the downwardly hanging front portion is brought forwards between the wearer's legs and then upwards so that its front edge will lie level with the upper edge of the waist belt, whereafter the fastener elements 16, 17 on the inside of the front part of the incontinence guard are pressed into fastening abutment with the fastener elements 12, 13 on the tapering parts 10, 11 of the front portions of the belt 1.

After the front part of the incontinence guard has been fastened to the waist belt, that part of the waist belt which is located between the respective attachment points 5, 6 and 16, 17 on the rear-edge part and front-edge part of the incontinence guard has no actual function, since the front-edge parts and rear-edge parts of the incontinence guard are able to function as parts of a waist band just as well as corresponding parts of the waist belt. Consequently, the strength of the connection 12, 14 need only be sufficient to hold the rear part of the incontinence guard in place as the incontinence guard and waist belt are put on. Thus, it is only necessary to dimension the fastener elements 16, 17 to provide an optimal strength in combination with the fastener elements 12, 13. This enables the fastener element 14 to be given smaller dimensions, therewith enabling narrow fastener elements 12, 13 to be used. The length of the fastener elements 16, 17, i.e. their extension in the longitudinal direction of the fastener elements 12, 13, may be adapted so as to obtain the requisite strength in the connections 12, 16 and 13, 17 respectively. FIG. 1 illustrates an embodiment which includes two fastener elements on respective rear-edge and front-edge portions of the incontinence guard 7. Because the fastener elements 12, 13 on the front portions of the waist belt extend over essentially the full length of the tapering portions 10, 11, it is possible to mount more than two fastener elements on the front part of the incontinence guard, said elements being able to coact with the fastener elements 12, 13 irrespective of the extent to which the belt portions 10, 11 overlap one another in accordance with the different waist sizes of different wearers.

The invention thus provides a waist belt which is sufficiently broad in the hip region to afford good comfort to the wearer, but which tapers at its front portions and therewith affords a saving in material in comparison with earlier known belts of this kind that have generally uniform widths. In comparison with belts that are provided with loop-bearing material over the whole of their extension, the inventive belt further saves in cost because only parts of the belt are provided with loop-bearing material. This enables the belt to be produced from an inexpensive plastic material, such as polyethylene for instance. Furthermore, the loop-bearing material and the belt material may be chosen optimally for their respective functions, independently of each other.

The mutually coacting fastener elements are preferably comprised of hook-bearing material and loop-bearing material of the Velcro® fastener type. The loop-bearing material will suitably have a width of between 20–150 mm, preferably between 30–50 mm. The ends of the tapering portions of the front portions of the waist belt have essentially the same width as the loop-bearing material. This reduces the risk of the hook-bearing element on one of the front portions being incorrectly positioned when being fastened to a coacting fastener element on the other of said front portions. The elongated loop-bearing material will have a length of between 200–800 mm, preferably between 300–440 mm.

Figure 2:
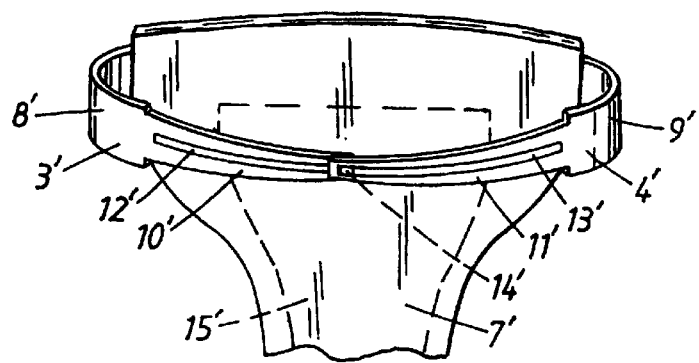
FIG. 2 is a schematic perspective view of a second embodiment of an inventive waist belt.
Figure 3:
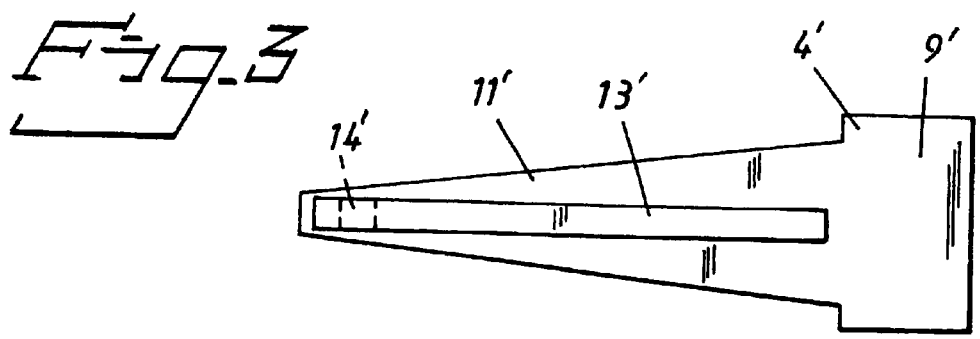
FIGS. 3–6 illustrate different embodiments of a waist belt front portion.

FIG. 2 illustrates schematically a second embodiment of a waist belt integrated in an incontinence guard 7'. The sole difference between this waist belt and the belt 1 illustrated in FIG. 1 is that the rear part of the belt is comprised of the rear-edge part of the incontinence guard. Those components of the FIG. 2 embodiment which find correspondence with the components of the FIG. 1 embodiment have been identified with the same reference signs although with the addition of a prime. The front portions 3', 4' of the waist belt are thus fastened directly to the side edges of the rear-part of the incontinence guard, e.g. glued or ultrasonically welded thereto. In other regards, the front portions of the waist belt shown in FIG. 2 are identical with the front portions shown in FIG. 1 and reference is made to the description of these portions with regard to the FIG. 2 embodiment. FIG. 3 illustrates a front portion 4' in larger scale.

Figure 4:
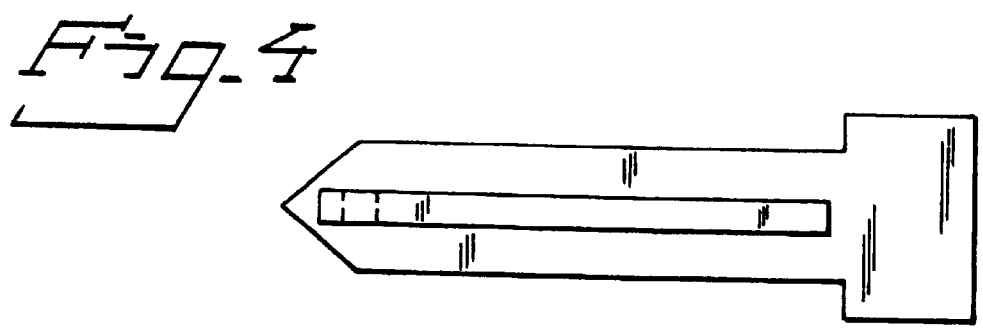
Figure 5:
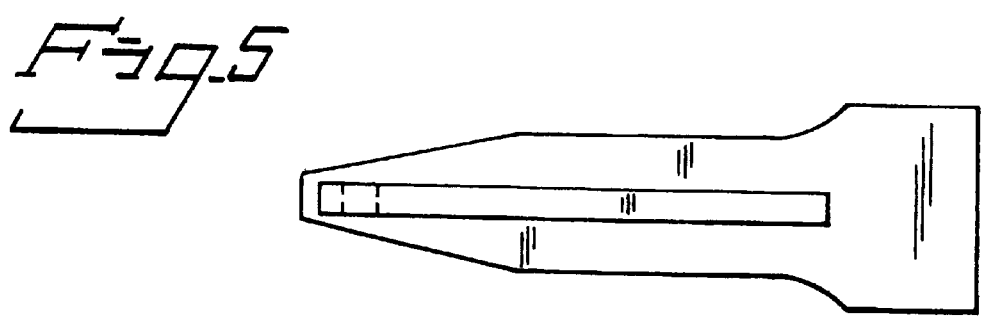
Figure 6:
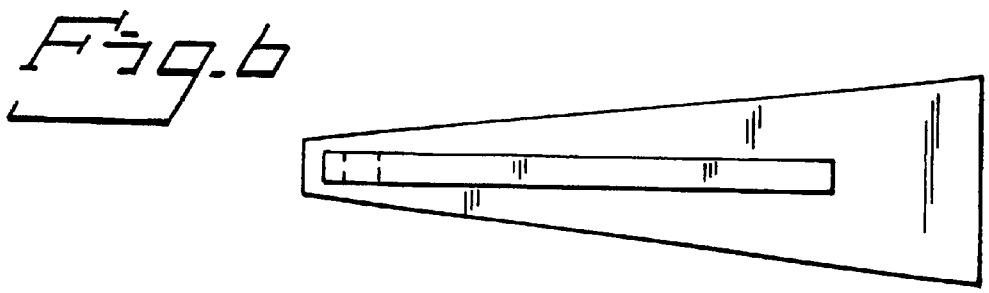

In the described embodiments, the front portions of a waist belt taper at first instantaneously and thereafter continuously to the ends of said portions. Although this configuration is preferred for manufacturing reasons of a technical nature, other configurations are conceivable. FIGS. 4–6 illustrate respectively feasible, although not preferred, configurations.

A preferred method of producing the front portions of a waist belt according to FIGS. 2 and 3 will now be described with reference to FIGS. 7 and 8.

A web 18 of flexible material, e.g. 1 mm thick nonwoven, is unreeled from a storage reel R and moved through two stations A and B with the aid of conveyor means (not shown), e.g. an endless belt conveyor. Elongated, rectangular strips 19 of fastener element material are placed on the web in station A with the longitudinal axes of said strips extending at right angles to the direction of web travel and at a specific distance apart, said strips being fastened to the web, e.g. glued thereto. The web is cut in station B in accordance with a repetitive cutting pattern. FIG. 8 illustrates from above a section of a web 18 that has passed through station B. As will be seen from FIG. 8, the cutting pattern includes two rows of short-side cuts S1, S2, each of which extends along an alternate short side of the strips 19 at a slight distance therefrom and on opposite sides of the strips 19. In the case illustrated in FIG. 8, the row of short-side cuts Si extend on the left side of the strips 19, whereas the row of short-side cuts S2 extend on the right side of the strips. The rows of short-side cuts S1, S2 are also displaced relative to one another, such that each strip 19 will have a short-side cut S1 or S2 along one of its short sides. The ends of mutually adjacent short-side cuts S1, S2 are joined together by cuts S3, S4. The cutting pattern also includes transverse cuts S5, S6 extending from the centre of each short-side cut and out to the nearest long edge of the web 18. As will be seen from FIG. 8, cutting of the web in the aforedescribed manner results in the formation of front portions 3', 4' of the waist belt shown in FIGS. 2 and 3.

Rows of fastener elements complementary to the fastener element strips 19 are attached in some suitable manner to the underside of the web 18 centrally opposite the end-parts of those ends of the strips along which short-side cuts S1 extend.

The aforedescribed method thus enables the front portions of a waist belt of the kind illustrated in FIG. 2 to be formed in a simple manner and essentially without waste, this latter contributing to the fact that such front portions can be produced relatively cheaply.

It will be understood that the aforedescribed method can be modified within the scope of the invention. For instance, the short-side cuts S1, S2 may be curved when desiring front portions with rounded ends. Further, the short-side cuts may extend longitudinally beyond the short sides of the strips when desiring the cuts S3, S4 to be located further away from the longitudinal edges of the strips 19 in those strip end parts that have short-side cuts along the short sides. The strip short sides need not be straight, but may alternatively be curved or triangular in shape. Such shapes are included by the term rectangular used in the claims. The invention is therefore restricted solely by the contents of the following claims.

What is claimed is:

1. A method of producing tapering front portions for a waist belt from a moving web of material, which comprises:

placing elongated first fastener elements on and fastening said elements to the web in a mutually sequential row and at a given distance apart with longitudinal axis of said elements extending perpendicularly to the direction of web travel;

cutting the web in accordance with a cutting pattern which includes:

a) mutually opposing rows of short-side cuts along each alternate short side of the first fastener elements, said rows being displaced relative to one another in the direction of web travel such that the short-side cuts relating to mutually adjacent first fastener elements are located along mutually opposing short sides;

b) transverse cuts which extend perpendicularly to the direction of web travel and from the center of each short-side cut in a direction away from the fastener elements; and c) connecting cuts which connect ends of said mutually opposing short-side cuts;

fastening second fastener elements intended for coaction with the first fastener elements to the web material in a row on the side opposite to the first fastener elements and centrally opposite end parts of the first fastener elements that face towards one of the rows of short-side cuts either before or after attaching the first fastener elements.

\* \* \* \* \*